United States Patent
Kelly et al.

(10) Patent No.: US 11,397,193 B2
(45) Date of Patent: Jul. 26, 2022

(54) MOVEMENT ANALYSIS METHOD AND APPARATUS

(71) Applicant: Koneksa Health Inc., New York, NY (US)

(72) Inventors: Peter John Kelly, London (GB); Robert David Ellis, London (GB); Chengrui Huang, New York, NY (US)

(73) Assignee: Koneksa Health Inc., New York, NY (US)

( * ) Notice: Subject to any disclaimer, the term of this patent is extended or adjusted under 35 U.S.C. 154(b) by 131 days.

(21) Appl. No.: 16/900,625

(22) Filed: Jun. 12, 2020

(65) Prior Publication Data
US 2021/0389342 A1 Dec. 16, 2021

(51) Int. Cl.
*G01P 13/00* (2006.01)
*G01P 15/08* (2006.01)

(52) U.S. Cl.
CPC .............. *G01P 13/00* (2013.01); *G01P 15/08* (2013.01)

(58) Field of Classification Search
CPC ................................ G01P 15/08; G01P 13/00
USPC ......................................................... 702/141
See application file for complete search history.

(56) References Cited

U.S. PATENT DOCUMENTS

| | | | |
|---|---|---|---|
| 10,330,491 B2 | 6/2019 | Janardhanan et al. | |
| 2003/0139692 A1 | 7/2003 | Barrey et al. | |
| 2006/0284979 A1 | 12/2006 | Clarkson | |
| 2012/0254934 A1* | 10/2012 | McBrearty | G16H 40/63 725/118 |
| 2014/0156215 A1 | 6/2014 | Eastman et al. | |
| 2014/0257535 A1 | 9/2014 | Morris et al. | |
| 2016/0217266 A1 | 7/2016 | Damani et al. | |
| 2017/0000384 A1 | 1/2017 | Annegarn et al. | |
| 2017/0095181 A1* | 4/2017 | Hauenstein | A61B 5/1121 |
| 2018/0192917 A1 | 7/2018 | Piijl et al. | |
| 2019/0104951 A1 | 4/2019 | Valys et al. | |
| 2019/0113364 A1 | 4/2019 | Khedr et al. | |
| 2020/0202117 A1* | 6/2020 | Wu | H04W 4/029 |
| 2020/0333137 A1 | 10/2020 | Cutri et al. | |

(Continued)

FOREIGN PATENT DOCUMENTS

EP    3459453 A1    3/2019

OTHER PUBLICATIONS

International Search Report for PCT/GB2021/051468 (dated Oct. 6, 2021).

(Continued)

*Primary Examiner* — Aditya S Bhat
(74) *Attorney, Agent, or Firm* — Merchant & Gould P.C.

(57) ABSTRACT

A method and apparatus are for movement analysis. The apparatus and method receive acceleration data from an accelerometer (or measurements from other motion sensors) that is carried by a user. The acceleration data is divided into epochs and a determination is made as to whether the user is walking or running within each epoch. Consecutive epochs in which the user is found to be walking may be concatenated to determine periods of time during which the user is walking or running. An initial estimate of the time that the user starts to walk or run and stops walking or running are determined for each period of walking. An iterative optimization process is then performed to determine accurate start and stop times for the period of walking or running.

30 Claims, 9 Drawing Sheets

(56) References Cited

U.S. PATENT DOCUMENTS

2021/0169374 A1* 6/2021 Vissiere .............. A61B 5/1126
2021/0389159 A1 12/2021 Kelly et al.

OTHER PUBLICATIONS

Karol Waga et al., "Detecting Movement Type by Route Segmentation and Classification", Colaborative computing: Networking, Applications and Worksharing (collaboratecom): 508-513 (2012).
International Search Report and Written Opinion for PCT/GB2021/051467 (dated Sep. 9, 2021).

* cited by examiner

MOVEMENT ANALYSIS METHOD AND APPARATUS

FIELD OF THE INVENTION

The present invention relates to the field of measurement of movement of a user. In particular, embodiments of the invention relate to a method and device for measuring the movement of a user to detect when the user is walking or running and to determine for how long the user is walking or running.

BACKGROUND

Devices such as activity monitors or pedometers are used to measure movements of a user. These devices can be used to determine when a user is walking and from this, the number of steps, or step count, of the user can also be determined. Accurate determination of the number of steps can be important for determining the correct amount of activity of a user.

Current devices are typically aimed at the leisure market—where accuracy is less important than repeatability. The devices may be dedicated devices designed to monitor the user's steps or they may take the form of a software application running on a user device such as a mobile (cellular) telephone or a smart watch or the like. As anyone who has used these devices will be aware, the different devices often give very different step counts even though the distance walked may be the same.

Current devices can inaccurately measure step count and walking periods of a user. In current approaches to movement measurement, sufficiently vigorous movement can be counted as a walking period. For example, where a device is wrist-worn, activities requiring movement of the wrist, such as chopping vegetables, can result in false readings. Existing approaches to measuring activity assume that the onset of any sufficiently vigorous movement constitutes the start time of the walking episode. Similarly, it is assumed that the cessation of sufficiently vigorous movement constitutes the end of the walking episode. On occasions this will overestimate the duration of walking if there are movements before the start of walking or after the end of walking that are sufficiently vigorous to meet the criteria but correspond to activities other than walking.

Accurate activity data may be critical for a variety of purposes, including medical applications. Additionally, certain clinically approved assessments require walking for a specific, pre-defined period. Any deviation from the required walking periods can nullify the assessment and affect the overall validity of the clinical trial. Therefore, for example, this data may be required for correlation with other sensors and time-specific measurements and the absence of accurate activity data may have a negative effect on determining the efficacy of therapies. For medical applications the requirement for accuracy is particularly important as it may affect treatment decisions and/or results of drug trials, which may have serious health consequences.

SUMMARY

Aspects of the invention are set out in the independent claims and preferred features are set out in the dependent claims.

A movement analysis method and apparatus are disclosed. The apparatus and method receive acceleration data from an accelerometer (or other motion data from a motion sensor) that is carried by a user. The data is divided into a sequence of epochs and a determination is made as to whether the user is walking within each epoch. Consecutive epochs in which the user is found to be walking may be concatenated to determine at least one period of time during which the user is walking. An initial estimate of the time that the user starts to walk and stops walking are determined for each period of walking based on the epoch times for the first and last epochs in the concatenated sequence. An iterative optimisation process is performed to determine accurate start and stop times for each period of walking.

According to one aspect, the invention provides an apparatus for determining start and stop times of a walking or running period of a user, the apparatus comprising at least one processor and memory configured to: obtain motion data from a user device that is carried by the user when walking or running; divide the motion data into a sequence of epochs; process the motion data in each epoch to determine one or more epochs in which the user is walking or running; determine at least one walking or running period of the user from said one or more epochs; determine an initial start time and an initial stop time for the determined walking or running period; and perform an iterative optimisation process that modifies the initial start time and/or the initial stop time to identify an optimised start time and/or stop time for the walking or running period that optimises a predefined optimisation function. The motion sensor may be an accelerometer or a gyroscope.

The iterative process may include: i) incrementing or decrementing the current candidate start time; ii) determining the value of a metric based on the incremented or decremented current candidate start time and the current candidate stop time; iii) determining if the metric determined in step ii) is better than the metric determined in step ii) at a preceding iteration and accepting the incremented or decremented start time as the current candidate start time and then returning to step i) if the metric determined in step ii) is better than the metric determined in the preceding iteration, and reverting to the preceding candidate start time if the metric determined in step ii) in the preceding iteration is better than the metric determined in the current iteration.

The iterative process may also include: i) incrementing or decrementing the current candidate stop time; ii) determining the value of a metric based on the incremented or decremented current candidate stop time and the current candidate start time; iii) determining if the metric determined in step ii) is better than the metric determined in step ii) at a preceding iteration and accepting the incremented or decremented stop time as the current candidate stop time and then returning to step i) if the metric determined in step ii) is better than the metric determined in the preceding iteration, and reverting to the preceding candidate stop time if the metric determined in step ii) in the preceding iteration is better than the metric determined in the current iteration.

Typically, the optimisation process is arranged to maximise or minimise a predetermined metric for the walking or running period. The metric may be arranged so that if the duration of the period of walking or running is extended (by changing either the start or the stop time), the metric will increase if the added interval corresponds to walking or running and will decrease if the added interval does not correspond to walking or running. The metric may also be arranged so that if the duration of the period of walking or running is reduced (by changing either the start or the stop time), the metric will increase if the removed interval does not correspond to walking or running and will decrease if the added interval does correspond to walking or running. In one embodiment, the metric depends upon the difference in time between the start time and the end time. The at least one processor and memory may be configured to determine an autocorrelation function of the acceleration data and wherein the metric comprises one or more parameters derived from the autocorrelation function. The parameters may be one or more of a peak value of the autocorrelation function after a zero-lag peak and an autocorrelation lag corresponding to the peak value.

The epochs are of a predetermined duration and typically overlap. In some embodiments, the at least processor and memory are configured to determine an autocorrelation function of the accelerometer data within each epoch and to determine if the user is walking or running within the epoch in dependence upon the autocorrelation function determined for the epoch. The at least one processor and memory may also be configured to determine one or more of stride period, stride correlation value and root-mean-square amplitude to determine if the user is walking or running within the epoch. The at least one processor and memory may be configured to determine if a user is walking or running within an epoch by determining one or more of: determining that the stride period is above a first threshold value and below a second threshold value; determining that the stride correlation value is above a third threshold value; and determining that the root-mean-square amplitude is above a fourth threshold value.

The at least one processor and memory may concatenate adjacent epochs of the sequence of epochs in which it is determined that the user is walking or running, to determine a walking or running period of the user; and may determine an initial start time and stop time for the determined walking or running period using the concatenated epochs.

The at least one processor and memory may determine the initial start time from an epoch time of the first epoch in the concatenated sequence of epochs corresponding to the walking or running period and may determine the initial stop time from an epoch time of the last epoch in the concatenated sequence of epochs corresponding to the walking or running period.

The at least one processor and memory may also be configured to obtain motion data from a plurality of motion sensors carried by the user when walking or running and the start time and stop time for the at least one walking or running period are determined using the motion data from the plurality of motion sensors. The processor and memory may determine a respective start and stop time for the at least one walking or running period using the motion data from each motion sensor and may: i) average the determined start and stop times for the at least one walking or running period; or ii) validate the start and stop times determined from the motion data from one sensor using the motion data or data derived from the motion data obtained from the other motion sensor. The motion sensors may form part of the same user device carried by the user or they may be mounted in different user devices carried by the user. Where the motion sensors are mounted in different user devices, they will typically be carried in different wear positions.

The invention also provides an apparatus for determining start and stop times of a walking or running period of a user, the apparatus comprising a processor and memory configured to: obtain acceleration data from a user device of the user; process the acceleration data to determine a walking or running period of the user; determine an initial start time and stop time for the determined walking or running period; and performing an iterative optimisation process that modifies the initial start time and stop time to identify a start time and a stop time for the walking or running period that optimises a predefined optimisation function to determine an optimised start time and stop time for the walking or running period.

According to another aspect, the invention provides a method for determining start and stop times of a walking or running period of a user, the method comprising: obtaining motion data from a user device that is carried by the user when walking or running; dividing the motion data into a sequence of epochs; processing the motion data in each epoch to determine one or more epochs in which the user is walking or running; determining at least one walking or running period of the user from said one or more epochs; determining an initial start time and an initial stop time for the determined walking or running period; and performing an iterative optimisation process that modifies the initial start time and/or the initial stop time to identify an optimised start time and/or stop time for the walking or running period that optimises a predefined optimisation function.

The invention also provides a tangible computer readable medium comprising computer implementable instructions for causing a programmable computer device to become configured as the apparatus summarised above.

The invention also provides a clinical trial system comprising a central computer that communicates with a plurality of user devices, each user device being arranged to collect acceleration data relating to movement of the user associated with the user device; and wherein the central computer or at least one user device comprises an apparatus as summarised above.

BRIEF DESCRIPTION OF THE DRAWINGS

Exemplary embodiments of the invention will now be described with reference to the accompanying figures in which.

DETAILED DESCRIPTION

Overview

As summarised above, the invention provides alternative ways for analysing a user's movements. The methods and devices provided by the invention can be used in various applications, such as in fitness trackers, performance management, and the like. However, the invention can also be used in a medical setting which will now be described.

Figure 1A:
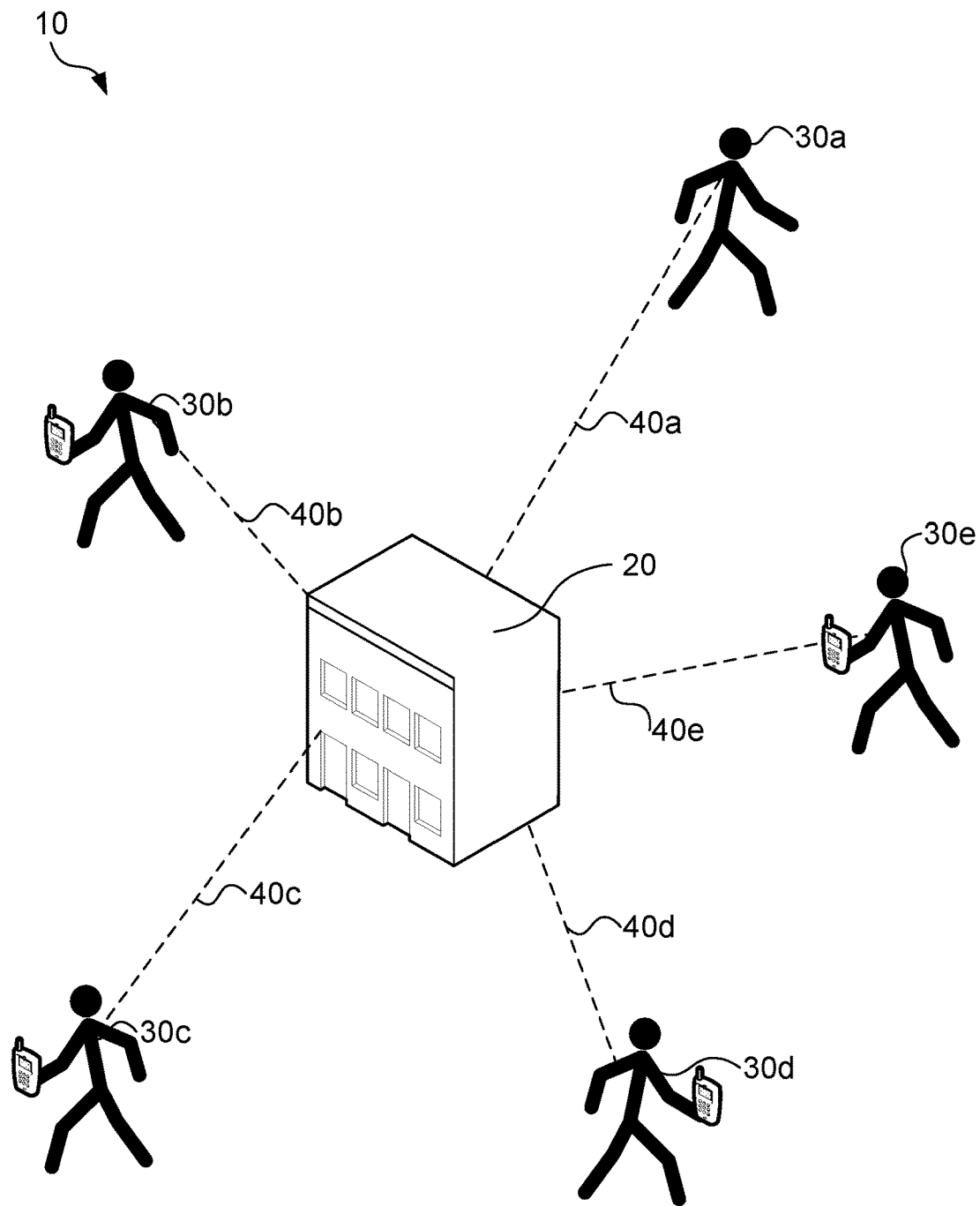
FIG. 1A schematically illustrates a clinical trial in which the movement of users taking part in the trial is determined by user devices worn or carried by the users and reported to a central server for collection and analysis.
Figure 1B:
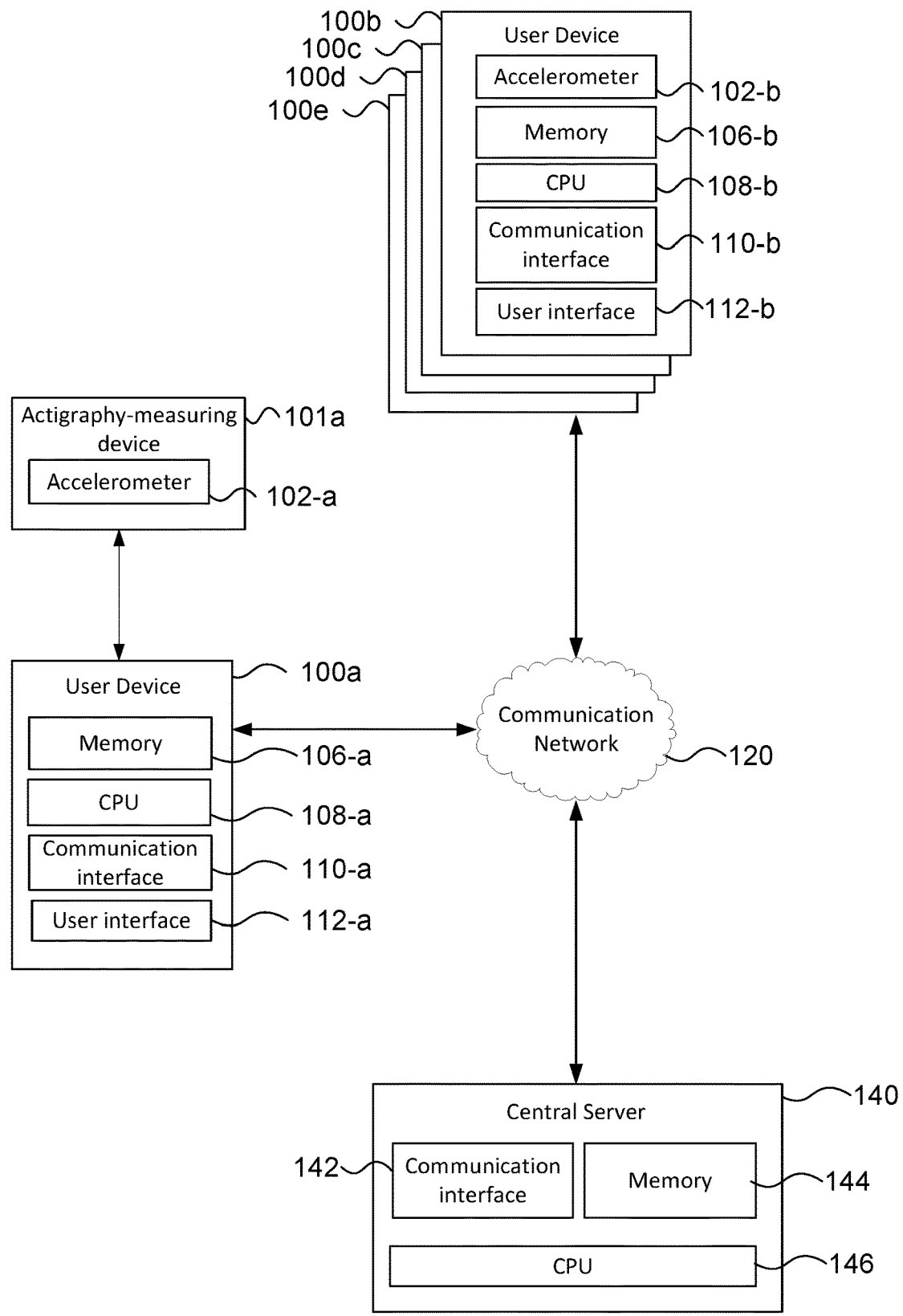
FIG. 1B is a block diagram illustrating the main electronic parts of the system shown in FIG. 1A.

More specifically, FIGS. 1A and 1B illustrate how the invention can be used in a clinical trial system 10 in which a number of patients (also referred to below as users) 30a to 30e use a respective user device 100a to 100e to monitor the movements of the corresponding patient when they are walking. The information gathered by the user devices 100 is transmitted over a communication network 120 (represented in FIG. 1A by the broken lines 40a to 40e) back to a central server 140 with results that may be displayed within the clinic 20.

The clinic 20 may be a health centre such as a hospital or doctor's surgery. It may comprise a single centre or a number of centres located in a number of different geographical locations. The patients 30a-30e are patients of the clinic 20 and are taking part in a medical trial, organised by the clinic 20. Each of the patients in the medical trial are cohorted into groups with the same medical condition.

Each of the patients 30a-30e is provided with a user device 100 that may be dedicated to the clinic and returned to the clinic after the trial is over. Alternatively, the clinic may provide the patient with a software application that they can run on their own user device—such as a cellular telephone or a smart watch or the like. In either case, each patient is asked to wear or carry their user device so that an accelerometer associated with the user device can capture the movements of the user during the clinical trial. As shown in FIG. 1B, some user devices 100 have a built-in accelerometer 102 but some (in this example user device 100a) do not. As an alternative, such as where the user device 100 does not have an accelerometer, a separate actigraphy-measuring device 101a is provided that has an accelerometer 102-a for capturing the movements of the patient 30a. The user device or the actigraphy-measuring device 101 is worn or carried by the patient, for example, around the patient's wrist, ankle, in a pocket, on a belt, held in a hand, placed in a bag worn by the patient or worn as a pendant, for example around the patient's neck.

Accelerometers typically provide acceleration information in three orthogonal directions which depend on the orientation of the accelerometer. By analysing the accelerometer data, the user device 100 can determine movement information about the patient which is then transmitted (wirelessly or over a wired connection) as patient data to the central server 140 for further analysis as part of the medical trial.

In one example, the patient data provided to the central server 140 comprises walking data and identification data that identifies the patient to which the walking data relates. The walking data may comprise one or more of: step count, walking or activity periods, distance walked, and calories burnt, over a period specified by the trial, for example a day, week, month or year. The patient data may be retrieved from the user device 100 when the patient visits the clinic, or the patient data may be transmitted to the clinic over a cellular or wired telephone or computer network (wirelessly or over a wired connection). Patient data collected at the clinic can be supplemented with physical observations and tests which can only be done at the clinic 20 and not monitored remotely. Accuracy of the data provided to the clinic 20 about a patient's activity outside of the clinic 20 and at home is important in ensuring that the medical trial receives a true representation of the patient's activity during the monitored period. This can help to determine the efficacy of the clinical trial's therapies.

In another example, the patient data provided to the central server 140 comprises the identification data for the patient together with the accelerometer data, so that the central server 140 processes the accelerometer data for each patient from which the central server 140 works out the walking data for each patient itself. Although not illustrated in FIG. 1B, in this case, the central server 140 further comprises a user interface including a user input device such as a keyboard, and/or software for processing the data collected from the user devices of the system.

The patient data indicating activity of the patient, such as walking data, is a good indicator of health or fitness levels of the patient. For example, it can be used as an indicator of recovery because step count is an indicator of general health. An increase in step count shows increased mobility, which can indicate a patient's improvement, whilst a decrease or stagnation of step count could indicate that a patient is not responding to treatment or is not showing an improvement, or even that a patient is getting more ill. In some cases, step count may be indicative of a need for a patient to be called into the clinic or could indicate that the patient may be required to spend a short amount of time in hospital. An increase in step count during time periods when the treatment's effects are greatest compared to when the effect of the treatment has worn off may give an indication of the efficacy of the treatment. In some examples, the collected patient data may be used by the clinic to help book appointments for the patient with a doctor or clinician as required.

The walking data provided by the user devices can also be used to provide one or more of the plurality of patients 30a-30e with personalised exercise plans, tailored to their individual needs and or capabilities as indicated by the data. For clinical trials, the walking data can be used to measure compliance with the trial protocols, capturing the required data and identifying non-compliant assessments. Prompts may be sent to a patient to request them to repeat assessments if required, encourage them to be active if their period of walking is insufficient or if their step count is too low, or identify broader health-related behavioural change recommendations.

Walking data is particularly useful to study in patients having one or more medical conditions which are known to affect walking capabilities. In some cases, temporary gait or balance complications may be caused by injury, trauma, inflammation or pain. In other cases, problems with walking such as gait, balance and coordination can be caused by specific conditions. Some of the conditions which may be particularly important in measuring walking activity include but are not limited to: arthritis, multiple sclerosis (MS), Meniere's disease, brain damage for example caused by a haemorrhage or tumour, Parkinson's disease, orthopaedic surgery on hips or lower body, cancer and associated therapies, cerebral palsy, obesity, gout, muscular dystrophy, stroke, spinal injury, deformities, etc.

The walking data can also be used for physical therapy measurement and performance management. Detailed analysis of walking data during targeted, timed assessments during managed or unmanaged therapy sessions activities can be provided to the patient or their therapists and doctors. That data can then be used to inform therapeutic regimens to improve recovery programs.

User Device

Figure 2:
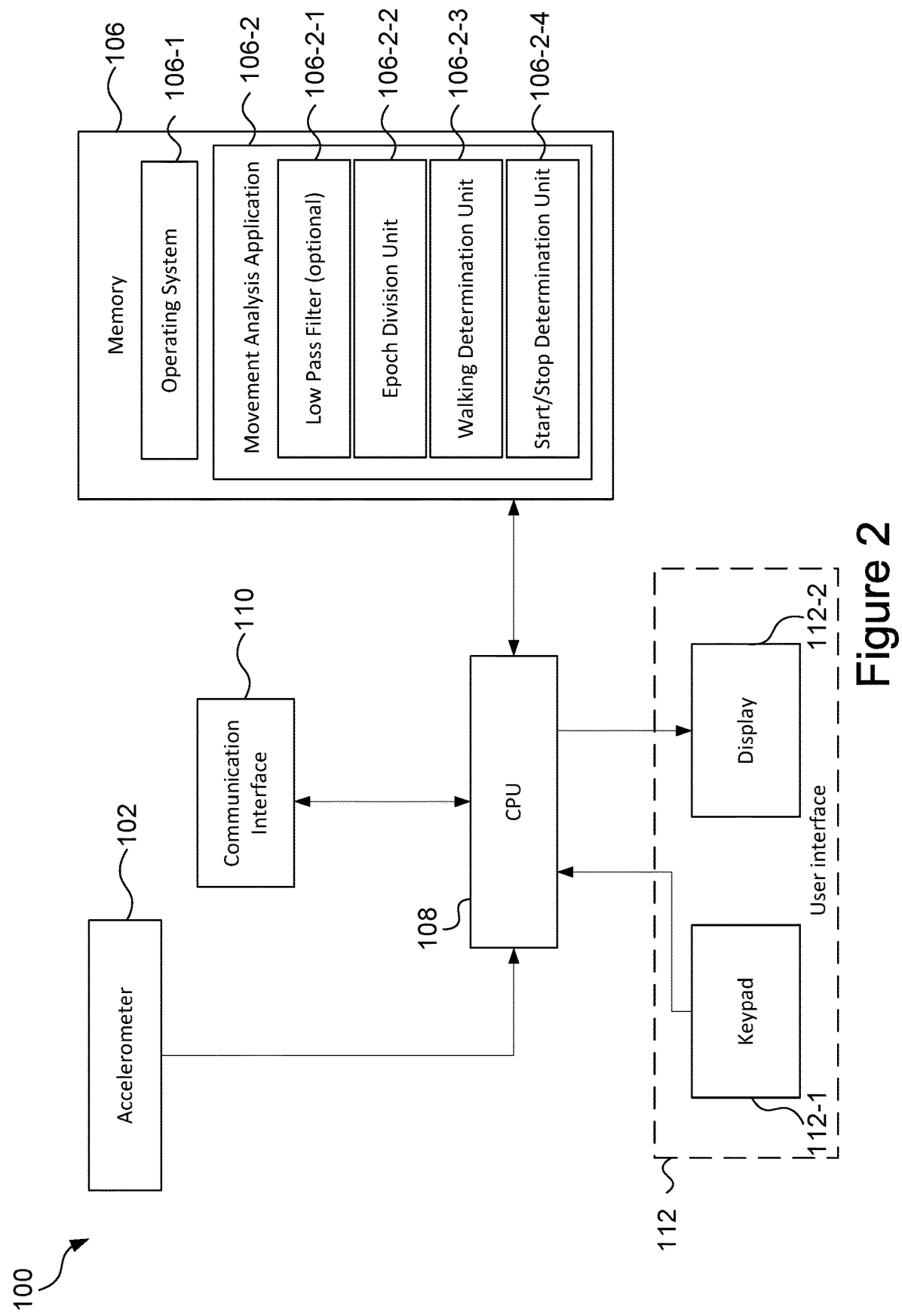
FIG. 2 is a block diagram illustrating the main components of a user device shown in FIG. 1B.

FIG. 2 is a block diagram of a typical user device 100 that is used in the system described above. As shown, in this case, the user device 100 has an accelerometer 102 that provides accelerometer data to at least one central processing unit (CPU) 108. The operation of the CPU 108 is controlled by software instructions that are stored in memory 106. As shown, the software instructions include an operating system 106-1 and a movement analysis application 106-2. The accelerometer data from the accelerometer 102 is processed by the movement analysis application 106-2 to work out the walking data for the patient.

The user device 100 also includes a communication interface 110 for communicating the patient data determined by the movement analysis application 106-2 to the central server 140; and a user interface 112 comprising a keypad 112-1 and a display 112-2 to allow the patient to interact with the user device 100. The display 112-2 may display one or more icons configured to provide information to the user and/or one or more of: time, date, number of steps, activity specific icons (walking running, cycling, etc.), activity duration, reminder messages and/or instructions concerning activity, network connection status, remaining battery power and any other useful information to be displayed to the user.

Movement Analysis Application—Overview

Figure 3:
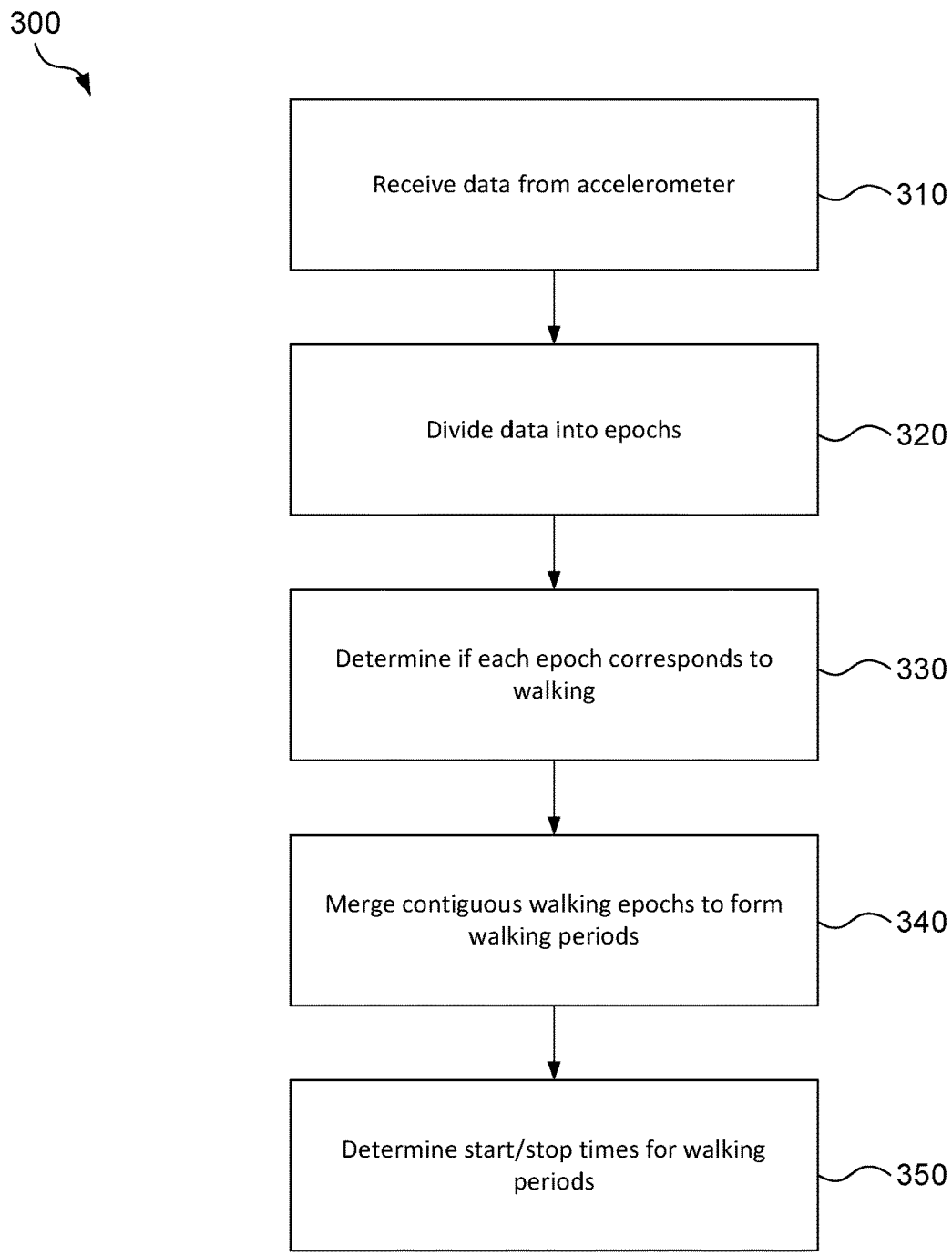
FIG. 3 is a flow diagram illustrating a prior art technique for determining the start and stop times of a period of walking of a user.

FIG. 3 illustrates an overview of the processing performed by the movement analysis application 106-2 on the accelerometer data in order to determine the start and stop times for periods in which the user is walking.

In step 310, data from the accelerometer 102 is received by the movement analysis application 106-2. The accelerometer data comprises a series of data points indexed by time, with the data point (reading) from the accelerometer at time t comprising acceleration measurements ($A_{Ax}(t)$, $A_{Ay}(t)$, $A_{Az}(t)$) in the three orthogonal directions: Ax, Ay and Az that are aligned with (defined by) the orientation of the accelerometer 102, rather than the orientation of the person carrying the accelerometer or any other geographic coordinate system. Readings from the accelerometer 102 are typically provided in units of g, where g is acceleration due to gravity at the Earth's surface (9.8 m/s$^2$). Sampling rates (the rate at which the accelerometer 102 provides the acceleration readings) will vary between accelerometers and are often configurable, but to be useful for analysing walking, the sampling rate should be at least 20 Hz, preferably higher (e.g. 30 Hz or 100 Hz).

If desired, the raw accelerometer data received in step 310 may be filtered by an optional low pass filter 106-2-1 to remove high frequency variations in the accelerometer measurements that are not associated with walking movement of the user. The cut off frequency of such a low pass filter is typically between 8 Hz and 20 Hz and preferably about 10 Hz.

At step 320 the vector accelerometry data received at step 310 (or after low pass filtering if performed) is divided into a sequence of epochs by an epoch division unit 106-2-2. An epoch is a predetermined division of time. In its simplest form, the data may be divided into a number of non-overlapping epochs: for example, for an epoch length of 5 seconds, the first epoch consists of the first 5 seconds, the second epoch consists of the next 5 seconds etc. However, this has the disadvantage of being sensitive to the positions of the epoch boundaries. An event that is split across two epochs may be detected less reliably than the same event that is wholly contained within a single epoch.

Figure 5:
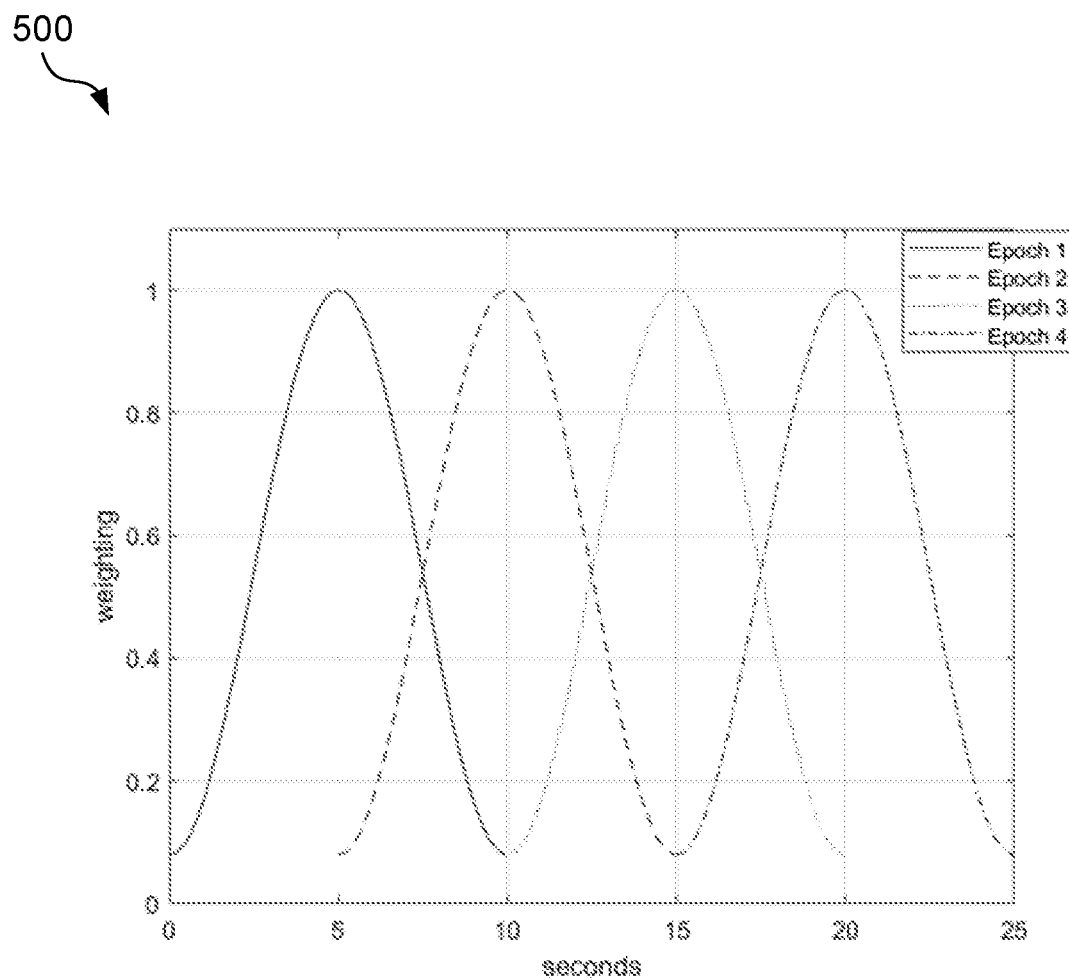
FIG. 5 illustrates a flow diagram illustrating a preferred technique for determining whether or not an epoch corresponds to walking.

Therefore, in the preferred embodiment, longer epochs are defined (typically between 5 and 20 seconds in duration) that overlap with the neighbouring epochs. For example, where the overlap is 50%, the first half of each epoch overlaps the previous epoch and the second half of each epoch overlaps the next epoch. The data within each epoch is weighted such that the data in the middle of the epoch are given the most weight, whilst the data at the start and end of each epoch is given less weight. A Hamming window may be used to achieve this although other window functions can be used such as, for example, Bartlett, Hanning, tapered cosine, etc. FIG. 5 illustrates a graphical representation of Hamming windows for four consecutive epochs. The graph shows overlapping Hamming windows that may be used to split and weight the data. Each of the four epochs is 10 seconds long and starts 5 seconds after the previous epoch starts (i.e. epoch 1 begins at 0 s and ends at 10 s, epoch 2 begins at 5 s and ends at 15 s, etc.). There is a 50% overlap between neighbouring epochs, resulting in epochs beginning at 5 second intervals. Each epoch has an associated time (referred to below as epoch time) which may correspond, for example, to the start time of the epoch, the end time of the epoch or the time of the middle of the epoch. As will be described in more detail below, this epoch time is used to identify approximate start and stop times for a period of walking.

The length of each epoch should be approximately equal to or less than the granularity of walking detection that is required. For example, if it is desired to detect walking periods that are as short as 10 seconds, then an epoch length of about 10 seconds should be used. However, the epoch length must be at least twice the expected stride period, i.e. at least about 2 seconds. Also, it should be noted that short epoch lengths (e.g. 2 or 3 seconds) are likely to have lower signal-to-noise ratio than longer epoch lengths (e.g. 10 seconds). However, the longer the epochs are chosen to be, the greater the risk that the user's walk parameters (in particular the stride period) are not constant over the epoch duration which can result in other inaccuracies. In practice, the inventors have found that epoch lengths of about 10 or 20 seconds work well for a variety of patients with a variety of physical conditions with an accuracy that meets or exceeds standards for clinical trial accuracy.

At step 330 a walking determination unit 106-2-3 analyses the weighted acceleration data in each of the epochs to determine whether the data indicates that the user is walking within that epoch. At step 340, a start/stop determination unit 106-2-4 merges consecutive epochs that have been determined to correspond to walking of the user and in step 350, determines a start and stop time for the merged epochs. The start time corresponds to the epoch time of the first epoch of the merged epochs (where the first epoch is the first of the series of merged epochs in which it was determined that the data in said epoch corresponds to walking, as determined in step 330); and the stop time corresponds to the epoch time of the final epoch of the merged epochs (where the final epoch is the last one of the series of merged epochs in which it was determined that the data in said epoch corresponds to walking). Where a walking period corresponds to a single epoch, the walking determination unit 106-2-3 may use the start time of the epoch as the start time and the end time of the epoch as the end time. However, since the Hamming window function reduces the effect of the first and last quarter of the epoch, the start time may instead be defined by the time of the start of the second quarter of the epoch and the end time may be defined by the time of the end of the third quarter of the epoch.

Movement Analysis Application—Walking Determination Unit

Figure 4:
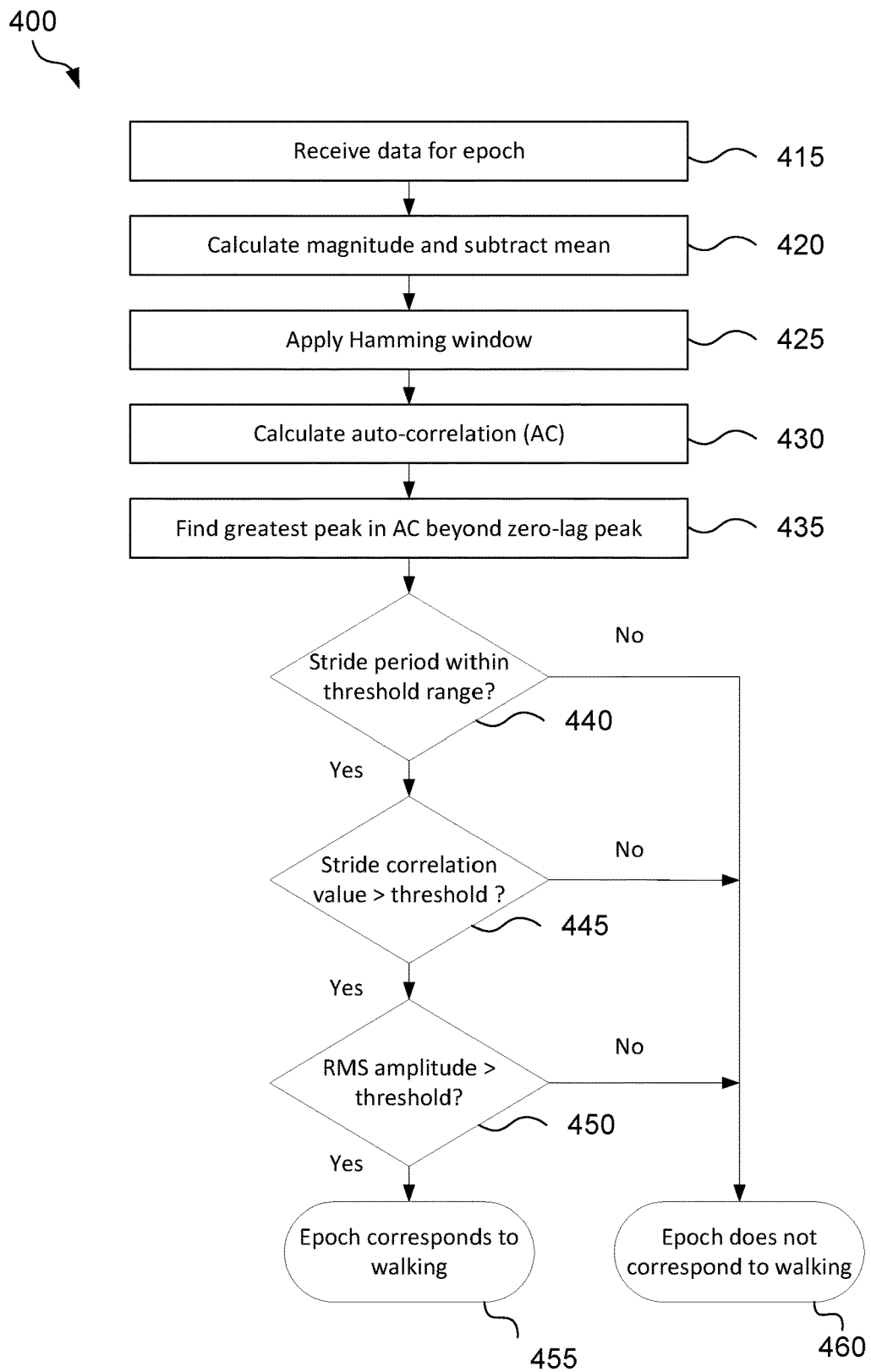
FIG. 4 is a graphical representation illustrating Hamming windows that are applied to four consecutive epochs, illustrating the overlapping nature of the epochs that are analysed.

A more detailed description will now be given with reference to FIGS. 2, 4 and 6 of the processing performed by the walking determination unit 106-2-3.

At step 415, the walking determination unit 106-2-3 receives the data for a current epoch that has been extracted from the accelerometer data by the epoch division unit 106-2-2. At step 420 the walking determination unit 106-2-3 determines the magnitude of the accelerometer data within the epoch as: $A_{mag}(t)=\text{sqrt}(A_{Ax}(t)^2+A_{Ay}(t)^2+A_{Az}(t)^2)$. The magnitude is calculated because the magnitude of acceleration is independent of the orientation of the accelerometer. In step 420, the walking determination unit 106-2-3 also subtracts from these magnitudes the mean of the magnitudes:

$$A_{mean}^{epoch} = 1/N \sum_{n=1}^{N} A_{mag}(n)$$

Where $A_{mag}(n)$ is the accelerometer data point at time n within the epoch; N is defined by the sample rate of the accelerometer and the length of the epoch over which the mean is computed. It is expected that the mean value of the magnitude signal will be close to 1 g (where g is the acceleration due to gravity at the Earth's surface), as gravity is the largest static component of acceleration measured by the accelerometer 102.

At step 425 the walking determination unit 106-2-3 then applies the above described Hamming window to the resulting data $(A_{mag}(t)-A^{epoch}_{mean})$. At step 430, the walking determination unit 106-2-3 calculates an autocorrelation function on the windowed data obtained at step 425 to detect periodic patterns in the epoch data. Specifically, the walking determination unit 106-2-3 calculates the following autocorrelation function of the epoch data:

$$AC(k) = \sum_{n=1}^{N-k} A^*_{mag}(n) \cdot A^*_{mag}(n-k)$$

Where $AC(k)$ is the autocorrelation at lag k; and $A^*_{mag}(n)$ is the Hamming windowed data at time n, i.e.:

$$A_{mag}*(n)=W(n)(A_{mag}(n)-A_{mean}^{epoch})$$

Where W(n) is the Hamming window function which is multiplied with $(A_{mag}(n)-A^{epoch}_{mean})$. In step 435, the walking determination unit 106-2-3 processes the autocorrelation values to determine the lag where the highest peak after the zero-lag peak (the zero-lag peak is defined as the part of the autocorrelation function between zero-lag and the first point at which the autocorrelation function is less than zero) is to be found in the autocorrelation function. The calculated lag corresponds to either the user's stride period or the user's step period. To illustrate this calculation, FIG. 6 is a plot representing the autocorrelation function that is determined in step 430 for one epoch. The auto-correlation function is symmetric about zero-lag (k=0) and only the part corresponding to non-negative lags is shown in the plot. The peaks corresponding to the stride and step periods are marked with a circle and a square respectively. The typical stride period is between 1.0 and 1.2 seconds (100-120 steps per minute) and the typical step period will be half of this value.

Figure 6:
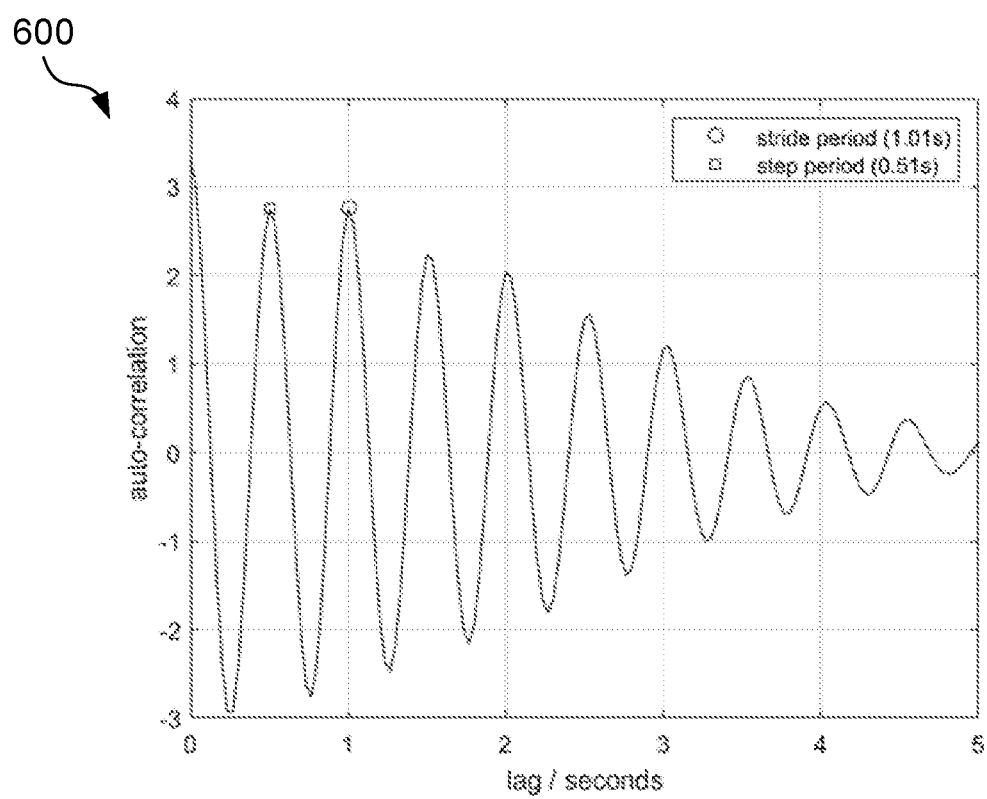
FIG. 6 is a plot illustrating an autocorrelation function calculated from the accelerometer data obtained whilst the user is walking.

In the example autocorrelation function illustrated in FIG. 6, the peak in the autocorrelation function at a lag of 0.5 seconds is almost as high as the peak in the autocorrelation function at a lag of 1.0 seconds and a slight variation in the accelerometer data might change which peak is the highest and therefore which peak is identified as the highest peak in step 435.

As the autocorrelation function is calculated at a plurality of defined lags, the autocorrelation values that are calculated may not include the autocorrelation value exactly at the peak. A potentially more accurate estimate for the lag corresponding to the peak in the autocorrelation function can be determined using interpolation. This can be achieved, for example, by fitting a second-order polynomial to the calculated peak value and its neighbour on either side, and taking the peak of the polynomial function as the peak of the autocorrelation function to work out a more accurate value of the lag corresponding to the highest peak.

Depending on how symmetric the user's gait is and also the wear position of the accelerometer, the peak identified may correspond to either the step or the stride period. For example, assuming the subject's gait is symmetric, if the device is worn/held centrally to the body, e.g. a phone held in front of the chest, or a device attached to the small of the subject's back, then a left step and a right step will produce very similar magnitude of acceleration at the device and the period calculated is likely to correspond to the step period. On the other hand, if the device is attached to an ankle or wrist, then the left and right steps may result in substantially different acceleration data and the period calculated is likely to correspond to the stride period.

There are various methods that can be used to resolve this ambiguity. For example, a thresholding technique can be used to determine whether the identified peak corresponds to the user's stride period or the step period based on the expected stride period and based on the step period being expected to be half the stride period etc. However, a further description of these techniques is not given as this is not essential to the present invention.

At step 440, having established whether the highest peak corresponds to the user's step period or the user's stride period, the walking determination unit 106-2-3 determines if the user's stride period (which equals the lag of the highest peak if the peak corresponds to the stride period or twice the lag of the highest peak if the peak corresponds to the step period), is within a predetermined range typical for walking (for example between 0.8 seconds and 1.25 seconds). If the user's stride period falls within the predetermined range, the process continues to step 445. If the user's stride period falls outside the predetermined range, walking determination unit 106-2-3 determines in step 460 that in the current epoch the user is not walking. Of course, a similar determination could be done instead (or in addition) using the step period.

At step 445 the walking determination unit 106-2-3 calculates a stride correlation value for the epoch. This is defined as the ratio of the value of the autocorrelation function at the calculated stride period to the value of the autocorrelation function at zero lag (k=0). If the stride correlation value is greater than a threshold value, the process continues to step 450. If the stride correlation value is below the threshold value, then the walking determination unit 106-2-3 determines in step 460 that in the current epoch the user is not walking. The threshold used may be determined by processing training data for which it is known whether or not the user is walking. Typical values for this threshold are between 0.2 and 0.8 and the inventors found that a threshold 0.4 works well.

At step 450, the walking determination unit 106-2-3 determines whether the root-mean-square (RMS) amplitude (or some other amplitude function) of the signal used as input to the auto-correlation function (i.e. the signal $A^*_{mag}(n)$ obtained from step 425) is greater than a threshold. If the RMS amplitude is greater than the threshold value, the process continues to step 455 where the walking determination unit 106-2-3 determines that the current epoch corresponds to walking. If the value of the RMS amplitude is below the threshold value, then the walking determination unit 106-2-3 determines in step 460 that in the current epoch the user is not walking. The threshold value used in step 450 is typically between 0.01 g and 0.1 g and the inventors have found that a value of 0.04 g works well.

Movement Analysis Application—Start/Stop Determination Unit

The above process identifies which epochs correspond to walking and which do not. Each walking epoch may then be analysed independently to extract scores for pertinent features, such as number of steps taken, speed and distance travelled. Alternatively, adjoining or contiguous walking epochs may be concatenated to form longer periods of walking. When concatenating, a limit may be set on the maximum duration of a walking period. For example, if a subject is walking for 10 minutes it is likely that the walking feature scores will not be constant over that time-span, so it may be desirable to split the 10 minutes into 30-second intervals and calculate feature scores for each 30-second interval.

From the epoch times of the first and last epoch in each concatenated sequence, a determination can be made (by the start/stop determination unit 106-2-4) of approximate start and stop times of each period of walking. If the epoch length is 10 seconds long with 50% overlap, the granularity/accuracy of the start and stop times of walking will be about 5 or 10 seconds. In many applications of the current technology, this will be a sufficient level of accuracy. However, if it is desired to improve the accuracy of the start and stop times then epochs of shorter duration (e.g. 1 or 2 seconds) could be used to analyse and further refine the start and stop times. However, as discussed above, short epochs are more sensitive to noise and there is a minimum epoch duration (each epoch should span at least 2 stride periods) necessary to capture the walking features.

In order to improve on the accuracy of the start/stop time determination, without needing to reduce significantly the epoch duration, the inventors have devised an iterative routine that aims to identify the start and stop times that maximise a predefined metric. Different metrics can be used. However, the metric should have the following properties:

For time intervals that correspond to walking the metric will be higher than for periods which are not walking.

If the duration of a period of walking is extended (by changing either the start or the stop time), the metric will increase if the added interval corresponds to walking and will decrease if the added interval does not correspond to walking.

Conversely, if the duration of a period of walking is decreased, then the metric will decrease if the removed interval corresponds to walking and will increase if the removed interval does not correspond to walking.

Using the processing techniques described above with reference to FIG. 4, the metric for a pair of candidate start and stop times ($t_{start}$, $t_{stop}$) may be determined as follows:

The acceleration data between the candidate start and stop times are extracted

The magnitudes of the extracted data are calculated

The mean of the magnitudes is subtracted from the magnitudes

The Hamming window is applied

The autocorrelation function is calculated

The peak value of the highest peak in the autocorrelation function for lags in the range of 0.5 seconds to 2 seconds is determined (0.5 seconds to 2 seconds is the expected range for stride periods)

The lag of this highest peak is identified

Figure 7:
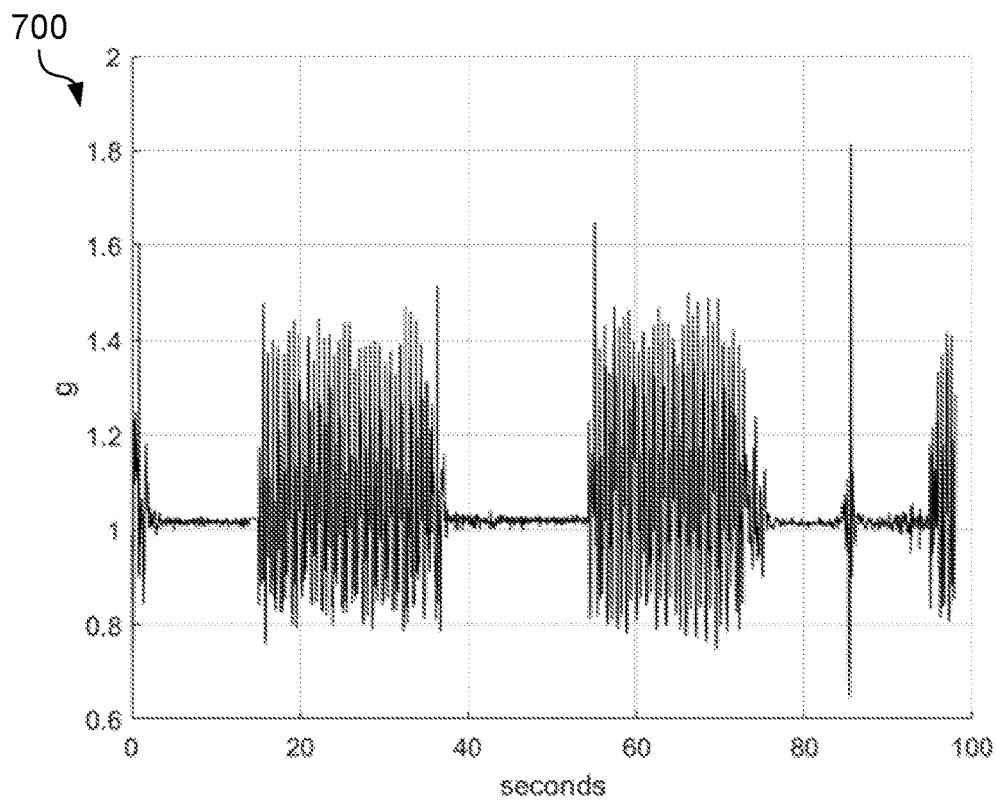
FIG. 7 illustrates a graphical representation of the magnitude of acceleration plotted against and illustrating periods of time when the user is moving.

The metric($t_{start}$, $t_{stop}$)=peak value/sqrt($t_{stop}$−$t_{start}$−lag) is calculated The way in which this metric can be used in the iterative procedure will now be explained for the example acceleration data shown in FIG. 7 that has two periods of walking and some other movements. Specifically, FIG. 7 is a plot of the magnitude of acceleration against time representing movement of a user. Periods of large acceleration correspond to movements of the user. There are two periods of movement that correspond to walking represented in the graph: from 15 until 37 seconds; and from 54 until 74 seconds. There are also movements which result in large magnitudes of acceleration but which do not correspond to walking. These movements are between 0 and 2 seconds; at 85 seconds; and between 95 and 98 seconds. From the graph alone, it is difficult to distinguish which of the accelerations correspond to walking and which do not. However, using the walking determination techniques described above and the above metric, it is possible to identify more accurately which periods correspond to walking and when those periods start and stop.

Figure 8:
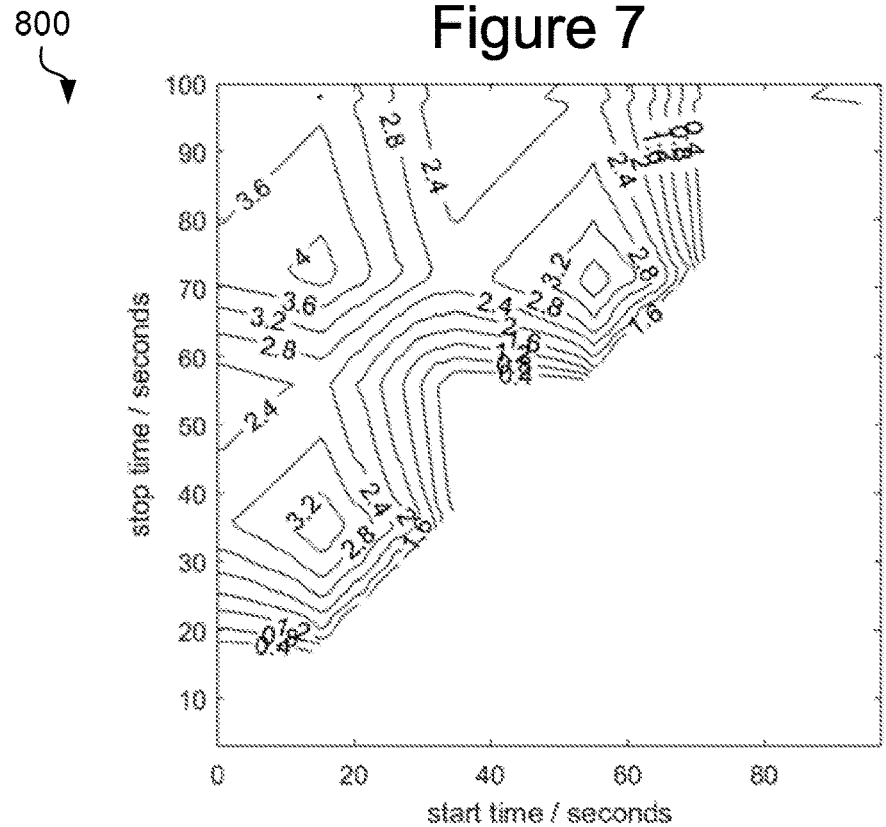
FIG. 8 illustrates a contour plot of a calculated metric that is used to determine start and stop times for a user walking.

Specifically, if the above metric is calculated for all possible start and stop times and plotted in a contour plot, the periods corresponding to walking appear as peaks in the contour plot which can be used to identify the start and stop times for the walking periods. This is illustrated in the contour plot shown in FIG. 8 which is calculated for the example acceleration data illustrated in FIG. 7. As shown in FIG. 8, the contour plot has three peaks, which identify start and stop times of periods that may correspond to walking—start/stop times of 15/37 seconds; 55/73 seconds; and 15/73 seconds. The first two peaks in the contour plot represent the two periods of walking in FIG. 7 and the third peak (with start time 15 seconds, stop time 73 seconds) represents the amalgam of the two walking periods. (Contours have not been drawn for the bottom right triangle of FIG. 8 as this would represent the case where the start time is later than the stop time.) Thus, by combining the walking determination described above and the information from this contour plot, it is possible to identify which periods correspond to walking and determine accurate start and stop times for those periods.

Figure 9:
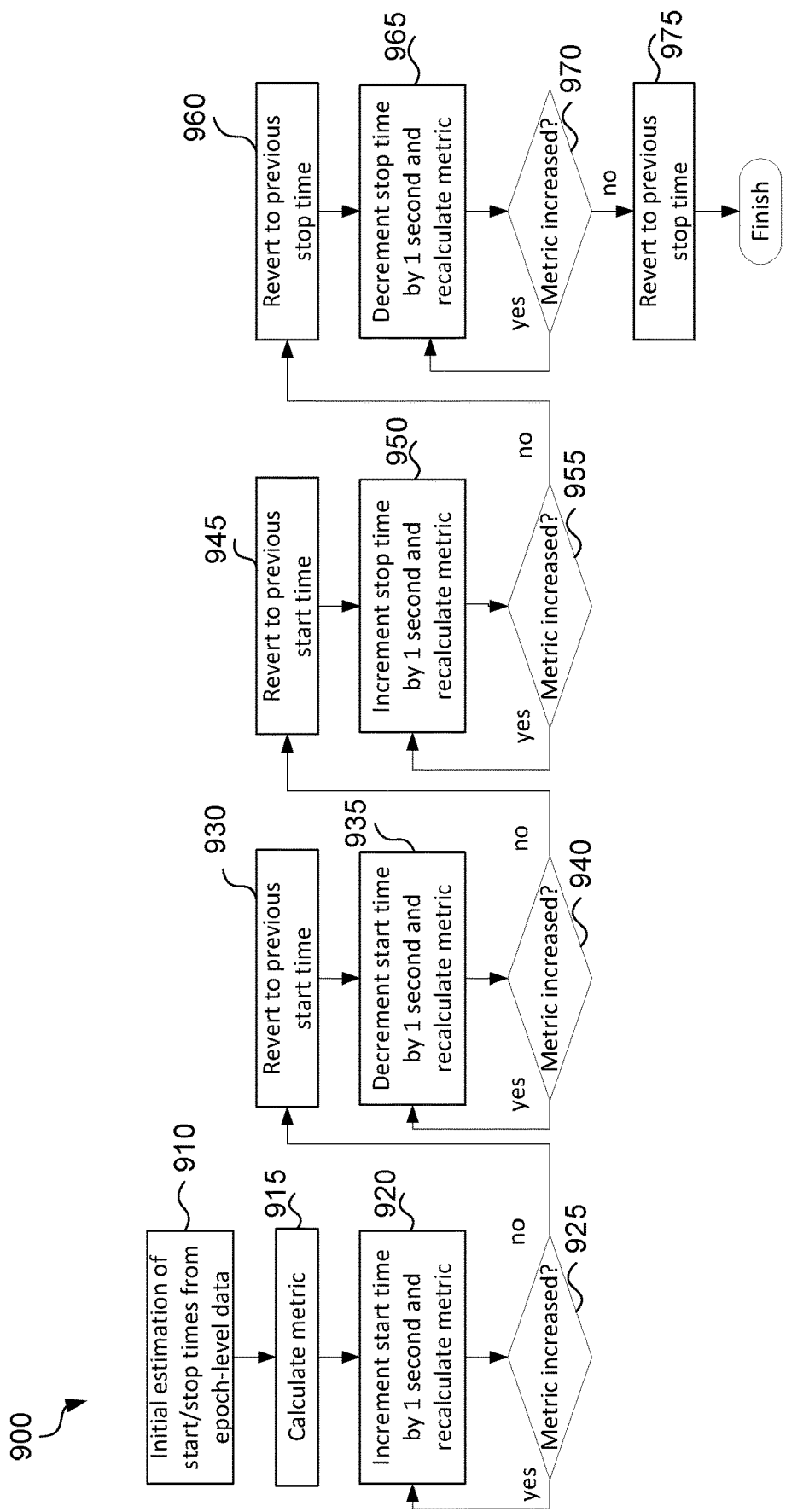
FIG. 9 illustrates a flow diagram for determining accurate start and stop times of a walking period using an iterative procedure.

In practice it is not necessary to calculate the metrics corresponding to all possible pairs of start and stop times. The processing described above with reference to FIG. 4 can be used to identify the periods that correspond to walking and the approximate start and stop times for those periods. The above described metric can then be calculated for this initial candidate start and stop time pair and an iterative routine performed to find the start and stop times that maximise the metric in the vicinity of the initial candidate (i.e. that find the peak in the contour plot shown in FIG. 8 that is closest to the initial candidate start/stop time pair). Various iterative techniques can be used to perform this optimisation process. One example technique is described below with reference to FIG. 9. This optimisation process is performed by the start/stop determination unit 106-2-4.

At step 910 an initial estimate of the start/stop times are determined from the epoch times of the first and last epochs of a concatenated sequence of epochs for which the walking determination unit 106-2-3 determines the user is walking. As discussed above, if the epoch length is 10 seconds long with 50% overlap, the granularity/accuracy of the start and stop times of walking determined using the processing described above will be about 5 or 10 seconds. At step 915 the above metric is calculated for the initial estimate of the start and stop times. At step 920 the start time is incremented by a second and the metric is recalculated.

At step 925 it is determined if the recalculated metric has increased. If the metric has increased, then the processing returns to step 920, where the start time is incremented by another second and the metric recalculated. Once the metric stops increasing and starts decreasing (or if the metric decreased after incrementing the start time the first time), the processing reverts to the previous start time in step 930. A similar process is then performed in steps 935 and 940 to determine if decreasing the start time leads to an improved metric. Once it is found in step 940 that the metric does not increase (but decreases), the process reverts to the previous start time in step 945. This start time represents the accurate determination of the start time for the period of walking under consideration. The processing then goes on to steps 950, 955, 960, 965, 970 and 975 where a similar process is performed with respect to the stop time. This leads to the determination of the accurate stop time in step 975 and the process ends.

Each time the metric is calculated during the iterative process, the acceleration data is extracted between the new start and stop times, the magnitudes of the extracted acceleration data are determined, the mean is determined and subtracted from the magnitudes, the Hamming window is applied, the autocorrelation function is determined and the highest peak found after the zero-lag peak and then the metric calculated.

As an example of this iterative process, consider the acceleration data shown in FIG. 7 and the contour plot shown in FIG. 8. The initial estimates for the start and stop times for the period of walking between 15 and 37 seconds is determined from the epoch data to be 20 and 40 seconds respectively. Keeping the stop time fixed at 40 seconds, the start time is reduced from 20 to 19 to 18 seconds etc., calculating the metric for each reduced start time value until it is found that the metric ceases to increase and starts to reduce at 14 seconds. Thus, an optimal start time of 15 seconds is determined. The same process is then applied to the end of the walking period and it is found the metric is maximum for a stop time of 37 seconds.

Once the start/stop determination unit 106-2-4 has determined the accurate start and stop times, this information can then be output to the user on the display 112-2 and/or it may be transmitted together with other related walking data and an identifier to identify the user to whom the data relates to the central server 140 for use in the clinical trial.

Modifications and Variations

A detailed embodiment has been described above. Various modifications and changes can be made to the above embodiment. Some of these variations will now be described.

The above embodiment described one example of how an accurate determination of the start time and stop time for a period of walking is determined. Of course, various changes can be made to this iterative process. For example, the accurate stop time can be determined before the accurate start time is determined and the iterative process can decrement the times before incrementing the times if desired. Similarly, it is not necessary that the increment or decrement is one second. Other increments and decrements can be used.

The maximum found may only be a local maximum of the metric function, not the global maximum within the vicinity of the initial estimate. Having found the local maximum, a greater maximum can be searched for in its vicinity. For example when incrementing the stop time, rather than stopping the search as soon as the metric starts to decrease, the process of incrementing the stop time can be continued to see if a higher metric can be found. If a higher metric is found, this is accepted as the current best solution and the process is continued. The process is continued until some stopping condition is satisfied at which point the start and stop times corresponding to the highest metric found so far are accepted as the best solution. Examples of stopping conditions may be that current candidate stop time is more than a specified number of seconds later than the stop time corresponding to the highest metric; or that the metric of the current candidate stop time falls below a threshold relative to the best metric.

As an example consider the peak in FIG. 7 corresponding to a start time of 17 seconds and a stop time of 37 seconds. As the stop time is incremented, the metric will decrease. If the stopping criteria is that the candidate stop time can only be extended 20 seconds beyond the stop time of the highest metric found so far, then the candidate stop time will be incremented until it gets to 57 seconds, at which point the process will stop as the metric corresponding to a stop time of 37 seconds will be the highest found. If on the other hand, the candidate stop time can be extended 30 seconds, then the higher peak corresponding to a start/stop time of 15/73 seconds will be found and chosen as the best solution, merging the two walking periods (corresponding to start/stop times of 15/37 and 55/73 seconds) into a single walking period with start/stop time of 15/73.

The metric defined above is just an example. Other definitions for the metric are possible and may prove advantageous in different scenarios. For example, the metric described above is a special case of the more general form:

$$\text{Metric}(t_{start}, t_{stop}) = \frac{\text{peak value}}{(t_{stop} - t_{start} - \text{lag})^n}$$

where $0 <= n <= 1$. ($n = \frac{1}{2}$ in the embodiment described above.)

Values of n close to 1 will result in numerous short periods of walking: walking periods will only be merged to form a single longer period if the characteristics pertaining to walking of the periods are very similar. Similarly, a walking period will only be extended if the characteristics of the proposed extension are very similar to the original walking period. Values of n close to zero will result in a few periods of walking, each with a relatively long duration, even if the characteristics of the merged walking periods are not particularly similar.

In practice, the inventors have found that a value of $n = \frac{1}{2}$ represents a good compromise between these two extremes.

As a further alternative, the above metric could be inverted and instead of looking for the start and stop times that maximise the metric, the start and stop times that minimise the metric may be found.

In the above embodiment, the accurate start and stop times were calculated and used for providing data for a clinical trial. As those skilled in the art will appreciate, the techniques described can be used in other applications. For example, they can be used to provide more accurate information about the period of walking of a user for a fitness tracker and the like.

In the above embodiments, the device was configured to determine periods of walking of the user. By adjusting the thresholds and other parameters used (e.g. using a higher threshold for magnitude of acceleration, and shorter expected step/stride periods), the device could be configured to detect periods of running. Such a device would be of interest for athletes who wish to track accurate information about the training they are performing. Specifically, the start and stop times for periods of running can be used for athletic performance measurement and management. Detailed analysis of start and stop times during targeted assessments of athletic activities can be provided to the athletes or their trainers and coaches. That data can then be used to inform training regimens to improve athletic performance.

In the above embodiment, the walking determination unit 106-2-3 applied three metrics to determine if the user is walking in a given epoch (in steps 440, 445 and 450). As those skilled in the art will appreciate, other techniques could be used for determining if the user is walking (or running) within the epoch. For example, the determination could be performed using just one or two of the metrics used in steps 440, 445 and 450.

In the above embodiments, the accelerometer data obtained from the accelerometer was analysed by looking at the autocorrelation function of the data. The autocorrelation analysis is good at highlighting periodic changes in the acceleration data—caused by repetitive movements such as walking and running. Other kinds of analysis could be performed to identify these periodic changes (and the period thereof). For example, a Fourier Transform (or other frequency analysis such as a Discrete Cosine Transform) could be determined and analysed to identify peaks in the frequency domain representative of the step or stride period. In the above embodiment, the autocorrelation is recalculated from scratch every time the start or stop time is incremented or decremented. Since the start time or the stop time is only being incremented or decremented by a relatively small amount (one second in the above example), the data used to determine the autocorrelation function at the current iteration will share many of the calculations from the previous iteration. The autocorrelation value at a specific lag just needs some data values added to it (if the start time has been decremented or the stop time has been incremented) or subtracted from it (if the start time has been incremented or the stop time has been decremented). Therefore, it is not necessary to perform all the calculations again. It is also possible to reduce further the computational load by making the assumption that the lag of the highest peak after the zero-lag peak will not change greatly from one iteration to the next. So, the autocorrelation values may be determined only for lag values around the lag value identified for the highest peak (after the zero-lag peak) in the previous iteration.

In the above embodiment, the data from the accelerometer was used as the basis for the calculations. Other motion sensors that provide sensor signals that vary with the movement of the user as they walk or run could also be used. For example, the signals from a gyroscope may be processed in a similar manner to that described above to work out start and stop times fora period of walking or running.

Further, in the case that the user's device has multiple such sensors built into it, the data from each sensor may be analysed and the results combined (for example averaged) to work out more accurate or less noisy start and stop times. Similarly, where the user is carrying multiple devices (such as a cellular telephone) and an actigraph device, where both devices have a motion sensor (such as an accelerometer or gyroscope), the system can determine start and stop times using the data from both devices. The measurements from the two devices can then be averaged again to improve signal to noise ratio or the measurements from one device may be used to corroborate or validate the start and stop times determined from motion data obtained from the other device.

In the above embodiment, a software application for processing accelerometer data was provided in the user device. The same or similar software may be provided in the computer of the central server—so that the central server performs the above step/stride analysis. This software application may be provided as computer implementable instructions on a carrier signal or on a tangible computer readable medium. Alternatively, the functions of the software application may be defined in hardware circuits such as in FPGA or ASIC devices.

It will be appreciated from the above description that many features of the different examples are interchangeable and combinable. The disclosure extends to further examples comprising features from different examples combined together in ways not specifically mentioned. Indeed, there are many features presented in the above examples and it will be apparent to the skilled person that these may be advantageously combined with one another.

The present application also comprises the following numbered clauses:

1. An apparatus for determining start and stop times of a walking or running period of a user, the apparatus comprising at least one processor and memory configured to:
  obtain motion data from a user device that is carried by the user when walking or running;
  divide the motion data into a sequence of epochs;
  process the motion data in each epoch to determine one or more epochs in which the user is walking or running;
  determine at least one walking or running period of the user from said one or more epochs;
  determine an initial start time and an initial stop time for the determined walking or running period; and
  perform an iterative optimisation process that modifies the initial start time and/or the initial stop time to identify an optimised start time and/or stop time for the walking or running period that optimises a predefined optimisation function.

2. An apparatus according to clause 1, wherein the iterative process includes:
  i) incrementing or decrementing the current candidate start time;
  ii) determining the value of a metric based on the incremented or decremented current candidate start time and the current candidate stop time;
  iii) determining if the metric determined in step ii) is better than the metric determined in step ii) at a preceding iteration and accepting the incremented or decremented start time as the current candidate start time and then returning to step i) if the metric determined in step ii) is better than the metric determined in the preceding iteration, and reverting to the preceding candidate start time if the metric determined in step ii) in the preceding iteration is better than the metric determined in the current iteration.

3. An apparatus according to clause 1 or 2, wherein the iterative process includes:

i) incrementing or decrementing the current candidate stop time;

ii) determining the value of a metric based on the incremented or decremented current candidate stop time and the current candidate start time;

iii) determining if the metric determined in step ii) is better than the metric determined in step ii) at a preceding iteration and accepting the incremented or decremented stop time as the current candidate stop time and then returning to step i) if the metric determined in step ii) is better than the metric determined in the preceding iteration, and reverting to the preceding candidate stop time if the metric determined in step ii) in the preceding iteration is better than the metric determined in the current iteration.

4. An apparatus according to any preceding clause, wherein the optimisation process is arranged to maximise or minimise a predetermined metric for the walking or running period.

5. An apparatus according to clause 4, wherein the metric is arranged so that if the duration of the period of walking or running is extended (by changing either the start or the stop time), the metric will increase if the added interval corresponds to walking or running and will decrease if the added interval does not correspond to walking or running.

6. An apparatus according to clause 4 or 5, wherein the metric is arranged so that if the duration of the period of walking or running is reduced (by changing either the start or the stop time), the metric will increase if the removed interval does not correspond to walking or running and will decrease if the added interval does correspond to walking or running.

7. An apparatus according to any preceding clause, wherein the metric depends upon the difference in time between the start time and the end time.

8. An apparatus according to any preceding clause, wherein the at least one processor and memory are configured to determine an autocorrelation function of the motion data and wherein the metric comprises one or more parameters derived from the autocorrelation function.

9. An apparatus according to clause 8, wherein the at least one processor and memory are configured to determine a peak value of the autocorrelation function after a zero-lag peak and wherein the metric depends on the determined peak value.

10. An apparatus according to clause 9, wherein the at least one processor and memory are configured to determine an autocorrelation lag corresponding to the peak value and wherein the metric depends on the determined autocorrelation lag.

11. An apparatus according to any of clauses 1 to 10, wherein the epochs are of a predetermined duration.

12. An apparatus according to any of clauses 1 to 11, wherein adjacent epochs overlap.

13. An apparatus according to any of clauses 1 to 12, wherein the at least one processor and memory are configured to determine an autocorrelation function of the accelerometer data within each epoch and to determine if the user is walking or running within the epoch in dependence upon the autocorrelation function determined for the epoch.

14. An apparatus according to any of clauses 1 to 13, wherein the at least one processor and memory are configured to determine one or more of stride period, stride correlation value and amplitude measure to determine if the user is walking or running within the epoch.

15. An apparatus according to clause 14, wherein the at least one processor and memory are configured to determine if a user is walking or running within an epoch by determining one or more of:

determining that the stride period is above a first threshold value and below a second threshold value;

determining that the stride correlation value is above a third threshold value; and determining that the amplitude measure is above a fourth threshold value.

16. An apparatus according to any preceding clause, wherein the at least one processor and memory are configured to concatenate adjacent epochs of the sequence of epochs in which it is determined that the user is walking or running, to determine a walking or running period of the user; and to determine an initial start time and stop time for the determined walking or running period using the concatenated epochs.

17. An apparatus according to any preceding clause, wherein the at least one processor and memory are configured to determine the initial start time from an epoch time of the first epoch in the concatenated sequence of epochs corresponding to the walking or running period.

18. An apparatus according to any preceding clause, wherein the at least one processor and memory are configured to determine the initial stop time from an epoch time of the last epoch in the concatenated sequence of epochs corresponding to the walking or running period.

19. An apparatus according to any preceding clause, wherein the motion sensor is an accelerometer or a gyroscope.

20. An apparatus according to any preceding clause, wherein the at least one processor and memory are configured to obtain motion data from a plurality of motion sensors carried by the user when walking or running and the start time and stop time for the at least one walking or running period are determined using the motion data from the plurality of motion sensors.

21. An apparatus according to clause 20, wherein the at least one processor and memory are configured to determine a respective start and stop time for the at least one walking or running period using the motion data from each motion sensor and are configured: i) to average the start and stop times for the at least one walking or running period; or ii) to validate the start and stop times determined from the motion data from one motion sensor using the motion data or data derived from the motion data obtained from another motion sensor.

22. An apparatus according to clause 20 or 21, wherein the motion sensors are mounted in the same user device carried by the user or wherein the motion sensors are mounted in different user devices carried by the user.

23. An apparatus according to clause 22, wherein the motion sensors are mounted in different user devices carried by the user in different wear positions.

24. An apparatus for determining start and stop times of a walking or running period of a user, the apparatus comprising a processor and memory configured to:

obtain motion data from a user device of the user;

process the motion data to determine a walking or running period of the user;

determine an initial start time and stop time for the determined walking or running period; and perform an iterative optimisation process that modifies the initial start time and/or stop time to identify a start time and a stop time for the walking or running period that optimises a predefined optimisation function.

25. An apparatus for determining start and stop times of a walking or running period of a user, the apparatus comprising:
- means for obtaining motion data from a user device that is carried by the user when walking or running;
- means for dividing the motion data into a sequence of epochs;
- means for processing the motion data in each epoch to determine one or more epochs in which the user is walking or running;
- means for determining at least one walking or running period of the user from said one or more epochs;
- means for determining an initial start time and an initial stop time for the determined walking or running period; and
- means for performing an iterative optimisation process that modifies the initial start time and/or the initial stop time to identify an optimised start time and/or stop time for the walking or running period that optimises a predefined optimisation function.

26. A method for determining start and stop times of a walking or running period of a user, the method comprising:
- obtaining motion data from a user device that is carried by the user when walking or running;
- dividing the motion data into a sequence of epochs;
- processing the motion data in each epoch to determine one or more epochs in which the user is walking or running;
- determining at least one walking or running period of the user from said one or more epochs;
- determining an initial start time and an initial stop time for the determined walking or running period; and
- performing an iterative optimisation process that modifies the initial start time and/or the initial stop time to identify an optimised start time and/or stop time for the walking or running period that optimises a predefined optimisation function.

27. A tangible computer readable medium comprising computer implementable instructions for causing a programmable computer device to become configured as an apparatus according to any of clauses 1 to 25.

28. A clinical trial system comprising a central computer that communicates with a plurality of user devices, each user device being arranged to collect acceleration data relating to movement of the user associated with the user device; and wherein the central computer or at least one user device comprises an apparatus according to any of clauses 1 to 25 for analysing acceleration data.

The invention claimed is:

1. An apparatus for determining start and stop times of a walking or running period of a user, the apparatus comprising at least one processor and memory configured to:
- obtain motion data from a user device that is carried by the user when walking or running;
- divide the motion data into a sequence of epochs;
- process the motion data in each epoch to determine one or more epochs in which the user is walking or running;
- determine at least one walking or running period of the user from said one or more epochs;
- determine an initial start time and an initial stop time for the determined walking or running period; and
- perform an iterative optimisation process that modifies the initial start time and/or the initial stop time to identify an optimised start time and/or stop time for the walking or running period that optimises a predefined optimisation function;

wherein the iterative process includes:
i) incrementing or decrementing the current candidate start time;
ii) determining the value of a metric based on the incremented or decremented current candidate start time and the current candidate stop time; and
iii) determining if the metric determined in step ii) is better than the metric determined in step ii) at a preceding iteration and accepting the incremented or decremented start time as the current candidate start time and then returning to step i) if the metric determined in step ii) is better than the metric determined in the preceding iteration, and reverting to the preceding candidate start time if the metric determined in step ii) in the preceding iteration is better than the metric determined in the current iteration.

2. An apparatus for determining start and stop times of a walking or running period of a user, the apparatus comprising at least one processor and memory configured to:
- obtain motion data from a user device that is carried by the user when walking or running;
- divide the motion data into a sequence of epochs;
- process the motion data in each epoch to determine one or more epochs in which the user is walking or running;
- determine at least one walking or running period of the user from said one or more epochs;
- determine an initial start time and an initial stop time for the determined walking or running period; and
- perform an iterative optimisation process that modifies the initial start time and/or the initial stop time to identify an optimised start time and/or stop time for the walking or running period that optimises a predefined optimisation function;

wherein the iterative process includes:
i) incrementing or decrementing the current candidate stop time;
ii) determining the value of a metric based on the incremented or decremented current candidate stop time and the current candidate start time; and
iii) determining if the metric determined in step ii) is better than the metric determined in step ii) at a preceding iteration and accepting the incremented or decremented stop time as the current candidate stop time and then returning to step i) if the metric determined in step ii) is better than the metric determined in the preceding iteration, and reverting to the preceding candidate stop time if the metric determined in step ii) in the preceding iteration is better than the metric determined in the current iteration.

3. An apparatus for determining start and stop times of a walking or running period of a user, the apparatus comprising at least one processor and memory configured to:
- obtain motion data from a user device that is carried by the user when walking or running;
- divide the motion data into a sequence of epochs;
- process the motion data in each epoch to determine one or more epochs in which the user is walking or running;
- determine at least one walking or running period of the user from said one or more epochs;
- determine an initial start time and an initial stop time for the determined walking or running period; and
- perform an iterative optimisation process that modifies the initial start time and/or the initial stop time to identify an optimised start time and/or stop time for the walking or running period that optimises a predefined optimisation function;

wherein the at least one processor and memory are configured to determine an autocorrelation function of the motion data, wherein the optimisation process is arranged to maximise or minimise a predetermined metric for the walking or running period, and wherein the metric comprises one or more parameters derived from the autocorrelation function.

4. An apparatus according to claim 3, wherein the at least one processor and memory are configured to determine a peak value of the autocorrelation function after a zero-lag peak and wherein the metric depends on the determined peak value.

5. An apparatus according to claim 4, wherein the at least one processor and memory are configured to determine an autocorrelation lag corresponding to the peak value and wherein the metric depends on the determined autocorrelation lag.

6. An apparatus according to claim 3, wherein the motion sensor is an accelerometer or a gyroscope.

7. An apparatus according to claim 3, wherein the at least one processor and memory are configured to obtain motion data from a plurality of motion sensors carried by the user when walking or running and the start time and stop time for the at least one walking or running period are determined using the motion data from the plurality of motion sensors.

8. An apparatus according to claim 7, wherein the at least one processor and memory are configured to determine a respective start and stop time for the at least one walking or running period using the motion data from each motion sensor and are configured: i) to average the start and stop times for the at least one walking or running period; or ii) to validate the start and stop times determined from the motion data from one motion sensor using the motion data or data derived from the motion data obtained from another motion sensor.

9. An apparatus according to claim 7, wherein the motion sensors are mounted in the same user device carried by the user or wherein the motion sensors are mounted in different user devices carried by the user typically in different wear positions.

10. An apparatus according to claim 3, forming part of a clinical trial system comprising a central computer that communicates with a plurality of user devices, each user device being arranged to collect motion data relating to movement of the user associated with the user device; and wherein the central computer or at least one user device comprises the apparatus according to claim 3 for determining start and stop times of a walking or running period of a user.

11. An apparatus for determining start and stop times of a walking or running period of a user, the apparatus comprising at least one processor and memory configured to:
obtain motion data from a user device that is carried by the user when walking or running;
divide the motion data into a sequence of epochs;
process the motion data in each epoch to determine one or more epochs in which the user is walking or running;
determine at least one walking or running period of the user from said one or more epochs;
determine an initial start time and an initial stop time for the determined walking or running period; and
perform an iterative optimisation process that modifies the initial start time and/or the initial stop time to identify an optimised start time and/or stop time for the walking or running period that optimises a predefined optimisation function;
wherein the at least one processor and memory are configured to determine an autocorrelation function of the accelerometer data within each epoch and to determine if the user is walking or running within the epoch in dependence upon the autocorrelation function determined for the epoch.

12. An apparatus according to claim 11, wherein the optimisation process is arranged to maximise or minimise a predetermined metric for the walking or running period.

13. An apparatus according to claim 12, wherein the metric is arranged so that if the duration of the period of walking or running is extended (by changing either the start or the stop time), the metric will increase if the added interval corresponds to walking or running and will decrease if the added interval does not correspond to walking or running.

14. An apparatus according to claim 12, wherein the metric is arranged so that if the duration of the period of walking or running is reduced (by changing either the start or the stop time), the metric will increase if the removed interval does not correspond to walking or running and will decrease if the added interval does correspond to walking or running.

15. An apparatus according to claim 12, wherein the metric depends upon the difference in time between the start time and the end time.

16. An apparatus according to claim 11, wherein the at least one processor and memory are configured to determine one or more of stride period, stride correlation value and amplitude measure to determine if the user is walking or running within the epoch.

17. An apparatus for determining start and stop times of a walking or running period of a user, the apparatus comprising at least one processor and memory configured to:
obtain motion data from a user device that is carried by the user when walking or running;
divide the motion data into a sequence of epochs;
process the motion data in each epoch to determine one or more epochs in which the user is walking or running;
determine at least one walking or running period of the user from said one or more epochs;
determine an initial start time and an initial stop time for the determined walking or running period; and
perform an iterative optimisation process that modifies the initial start time and/or the initial stop time to identify an optimised start time and/or stop time for the walking or running period that optimises a predefined optimisation function;
wherein the at least one processor and memory are configured to determine if a user is walking or running within an epoch by determining one or more of:
determining that the stride period is above a first threshold value and below a second threshold value;
determining that the stride correlation value is above a third threshold value; and
determining that the amplitude measure is above a fourth threshold value.

18. An apparatus for determining start and stop times of a walking or running period of a user, the apparatus comprising at least one processor and memory configured to:
obtain motion data from a user device that is carried by the user when walking or running;
divide the motion data into a sequence of epochs;
process the motion data in each epoch to determine one or more epochs in which the user is walking or running;
determine at least one walking or running period of the user from said one or more epochs;
determine an initial start time and an initial stop time for the determined walking or running period; and perform an iterative optimisation process that modifies the initial start time and/or the initial stop time to identify an optimised start time and/or stop time for the walking or running period that optimises optimisation function;

wherein the at least one processor and memory are configured to concatenate adjacent epochs of the sequence of epochs in which it is determined that the user is walking or running, to determine a walking or running period of the user; and to determine an initial start time and stop time for the determined walking or running period using the concatenated epochs.

19. A method for determining start and stop times of a walking or running period of a user, the method comprising:
obtaining motion data from a user device that is carried by the user when walking or running;
dividing the motion data into a sequence of epochs;
processing the motion data in each epoch to determine one or more epochs in which the user is walking or running;
determining at least one walking or running period of the user from said one or more epochs;
determining an initial start time and an initial stop time for the determined walking or running period; and
performing an iterative optimisation process that modifies the initial start time and/or the initial stop time to identify an optimised start time and/or stop time for the walking or running period that optimises a predefined optimisation function;
wherein the iterative process includes:
i) incrementing or decrementing the current candidate start time;
ii) determining the value of a metric based on the incremented or decremented current candidate start time and the current candidate stop time; and
iii) determining if the metric determined in step ii) is better than the metric determined in step ii) at a preceding iteration and accepting the incremented or decremented start time as the current candidate start time and then returning to step i) if the metric determined in step ii) is better than the metric determined in the preceding iteration, and reverting to the preceding candidate start time if the metric determined in step ii) in the preceding iteration is better than the metric determined in the current iteration.

20. A method for determining start and stop times of a walking or running period of a user, the method comprising:
obtaining motion data from a user device that is carried by the user when walking or running;
dividing the motion data into a sequence of epochs;
processing the motion data in each epoch to determine one or more epochs in which the user is walking or running;
determining at least one walking or running period of the user from said one or more epochs;
determining an initial start time and an initial stop time for the determined walking or running period; and
performing an iterative optimisation process that modifies the initial start time and/or the initial stop time to identify an optimised start time and/or stop time for the walking or running period that optimises a predefined optimisation function,
wherein the iterative process includes:
i) incrementing or decrementing the current candidate stop time;
ii) determining the value of a metric based on the incremented or decremented current candidate stop time and the current candidate start time; and
iii) determining if the metric determined in step ii) is better than the metric determined in step ii) at a preceding iteration and accepting the incremented or decremented stop time as the current candidate stop time and then returning to step i) if the metric determined in step ii) is better than the metric determined in the preceding iteration, and reverting to the preceding candidate stop time if the metric determined in step ii) in the preceding iteration is better than the metric determined in the current iteration.

21. A method for determining start and stop times of a walking or running period of a user, the method comprising:
obtaining motion data from a user device that is carried by the user when walking or running;
dividing the motion data into a sequence of epochs;
processing the motion data in each epoch to determine one or more epochs in which the user is walking or running;
determining at least one walking or running period of the user from said one or more epochs;
determining an initial start time and an initial stop time for the determined walking or running period; and
performing an iterative optimisation process that modifies the initial start time and/or the initial stop time to identify an optimised start time and/or stop time for the walking or running period that optimises a predefined optimisation function,
wherein the processing includes determining an autocorrelation function of the motion data, wherein the optimisation process maximises or minimises a predetermined metric for the walking or running period and wherein the metric comprises one or more parameters derived from the autocorrelation function.

22. A method for determining start and stop times of a walking or running period of a user, the method comprising:
obtaining motion data from a user device that is carried by the user when walking or running;
dividing the motion data into a sequence of epochs;
processing the motion data in each epoch to determine one or more epochs in which the user is walking or running;
determining at least one walking or running period of the user from said one or more epochs;
determining an initial start time and an initial stop time for the determined walking or running period; and
performing an iterative optimisation process that modifies the initial start time and/or the initial stop time to identify an optimised start time and/or stop time for the walking or running period that optimises a predefined optimisation function,
wherein the processing includes determining an autocorrelation function of the accelerometer data within each epoch and determining if the user is walking or running within the epoch in dependence upon the autocorrelation function determined for the epoch.

23. A method for determining start and stop times of a walking or running period of a user, the method comprising:
obtaining motion data from a user device that is carried by the user when walking or running;
dividing the motion data into a sequence of epochs;
processing the motion data in each epoch to determine one or more epochs in which the user is walking or running;
determining at least one walking or running period of the user from said one or more epochs;
determining an initial start time and an initial stop time for the determined walking or running period; and performing an iterative optimisation process that modifies the initial start time and/or the initial stop time to identify an optimised start time and/or stop time for the walking or running period that optimises a predefined optimisation function, wherein the at least one processor and memory are configured to determine if a user is walking or running within an epoch by determining one or more of:

determining that the stride period is above a first threshold value and below a second threshold value;

determining that the stride correlation value is above a third threshold value; and determining that the amplitude measure is above a fourth threshold value.

24. A method for determining start and stop times of a walking or running period of a user, the method comprising:

obtaining motion data from a user device that is carried by the user when walking or running;

dividing the motion data into a sequence of epochs;

processing the motion data in each epoch to determine one or more epochs in which the user is walking or running;

determining at least one walking or running period of the user from said one or more epochs;

determining an initial start time and an initial stop time for the determined walking or running period; and performing an iterative optimisation process that modifies the initial start time and/or the initial stop time to identify an optimised start time and/or stop time for the walking or running period that optimises a predefined optimisation function, wherein the at least one processor and memory are configured to concatenate adjacent epochs of the sequence of epochs in which it is determined that the user is walking or running, to determine a walking or running period of the user; and to determine an initial start time and stop time for the determined walking or running period using the concatenated epochs.

25. A non-transitory tangible computer readable medium comprising computer implementable instructions for causing a programmable computer device to perform the method of:

obtaining motion data from a user device that is carried by the user when walking or running;

dividing the motion data into a sequence of epochs;

processing the motion data in each epoch to determine one or more epochs in which the user is walking or running;

determining at least one walking or running period of the user from said one or more epochs;

determining an initial start time and an initial stop time for the determined walking or running period; and performing an iterative optimisation process that modifies the initial start time and/or the initial stop time to identify an optimised start time and/or stop time for the walking or running period that optimises a predefined optimisation function, wherein the iterative process includes:

i) incrementing or decrementing the current candidate start time;

ii) determining the value of a metric based on the incremented or decremented current candidate start time and the current candidate stop time; and iii) determining if the metric determined in step ii) is better than the metric determined in step ii) at a preceding iteration and accepting the incremented or decremented start time as the current candidate start time and then returning to step i) if the metric determined in step ii) is better than the metric determined in the preceding iteration, and reverting to the preceding candidate start time if the metric determined in step ii) in the preceding iteration is better than the metric determined in the current iteration.

26. A non-transitory tangible computer readable medium comprising computer implementable instructions for causing a programmable computer device to perform the method of:

obtaining motion data from a user device that is carried by the user when walking or running;

dividing the motion data into a sequence of epochs;

processing the motion data in each epoch to determine one or more epochs in which the user is walking or running;

determining at least one walking or running period of the user from said one or more epochs;

determining an initial start time and an initial stop time for the determined walking or running period; and performing an iterative optimisation process that modifies the initial start time and/or the initial stop time to identify an optimised start time and/or stop time for the walking or running period that optimises a predefined optimisation function, wherein the iterative process includes:

i) incrementing or decrementing the current candidate stop time;

ii) determining the value of a metric based on the incremented or decremented current candidate stop time and the current candidate start time; and iii) determining if the metric determined in step ii) is better than the metric determined in step ii) at a preceding iteration and accepting the incremented or decremented stop time as the current candidate stop time and then returning to step i) if the metric determined in step ii) is better than the metric determined in the preceding iteration, and reverting to the preceding candidate stop time if the metric determined in step ii) in the preceding iteration is better than the metric determined in the current iteration.

27. A non-transitory tangible computer readable medium comprising computer implementable instructions for causing a programmable computer device to perform the method of:

obtaining motion data from a user device that is carried by the user when walking or running;

dividing the motion data into a sequence of epochs;

processing the motion data in each epoch to determine one or more epochs in which the user is walking or running;

determining at least one walking or running period of the user from said one or more epochs;

determining an initial start time and an initial stop time for the determined walking or running period; and performing an iterative optimisation process that modifies the initial start time and/or the initial stop time to identify an optimised start time and/or stop time for the walking or running period that optimises a predefined optimisation function, wherein the processing includes determining an autocorrelation function of the motion data, wherein the optimisation process maximises or minimises a predetermined metric for the walking or running period and wherein the metric comprises one or more parameters derived from the autocorrelation function.

28. A non-transitory tangible computer readable medium comprising computer implementable instructions for causing a programmable computer device to perform the method of:
- obtaining motion data from a user device that is carried by the user when walking or running;
- dividing the motion data into a sequence of epochs;
- processing the motion data in each epoch to determine one or more epochs in which the user is walking or running;
- determining at least one walking or running period of the user from said one or more epochs;
- determining an initial start time and an initial stop time for the determined walking or running period; and
- performing an iterative optimisation process that modifies the initial start time and/or the initial stop time to identify an optimised start time and/or stop time for the walking or running period that optimises a predefined optimisation function,
- wherein the processing includes determining an autocorrelation function of the accelerometer data within each epoch and determining if the user is walking or running within the epoch in dependence upon the autocorrelation function determined for the epoch.

29. A non-transitory tangible computer readable medium comprising computer implementable instructions for causing a programmable computer device to perform the method of:
- obtaining motion data from a user device that is carried by the user when walking or running;
- dividing the motion data into a sequence of epochs;
- processing the motion data in each epoch to determine one or more epochs in which the user is walking or running;
- determining at least one walking or running period of the user from said one or more epochs;
- determining an initial start time and an initial stop time for the determined walking or running period; and
- performing an iterative optimisation process that modifies the initial start time and/or the initial stop time to identify an optimised start time and/or stop time for the walking or running period that optimises a predefined optimisation function,
- wherein the at least one processor and memory are configured to determine if a user is walking or running within an epoch by determining one or more of:
- determining that the stride period is above a first threshold value and below a second threshold value;
- determining that the stride correlation value is above a third threshold value; and
- determining that the amplitude measure is above a fourth threshold value.

30. A non-transitory tangible computer readable medium comprising computer implementable instructions for causing a programmable computer device to perform the method of:
- obtaining motion data from a user device that is carried by the user when walking or running;
- dividing the motion data into a sequence of epochs;
- processing the motion data in each epoch to determine one or more epochs in which the user is walking or running;
- determining at least one walking or running period of the user from said one or more epochs;
- determining an initial start time and an initial stop time for the determined walking or running period; and
- performing an iterative optimisation process that modifies the initial start time and/or the initial stop time to identify an optimised start time and/or stop time for the walking or running period that optimises a predefined optimisation function,
- wherein the at least one processor and memory are configured to concatenate adjacent epochs of the sequence of epochs in which it is determined that the user is walking or running, to determine a walking or running period of the user; and to determine an initial start time and stop time for the determined walking or running period using the concatenated epochs.

* * * * *